United States Patent
Taheri

(10) Patent No.: US 6,585,761 B2
(45) Date of Patent: Jul. 1, 2003

(54) PROSTHETIC VEIN VALVE AND METHOD

(76) Inventor: Syde A. Taheri, 1275 Delaware Ave., Buffalo, NY (US) 14209

( * ) Notice: Subject to any disclaimer, the term of this patent is extended or adjusted under 35 U.S.C. 154(b) by 103 days.

(21) Appl. No.: 09/796,994

(22) Filed: Mar. 1, 2001

(65) Prior Publication Data

US 2002/0123800 A1 Sep. 5, 2002

(51) Int. Cl.$^7$ .................................................. A61F 2/06
(52) U.S. Cl. ..................... 623/1.24; 623/1.42; 623/2.33
(58) Field of Search ............................... 623/1.26, 1.43, 623/2.18, 2.33, 2.2, 2.21, 1.42, 2.12–2.19

(56) References Cited

U.S. PATENT DOCUMENTS

| | | | |
|---|---|---|---|
| 4,851,001 A | * 7/1989 | Taheri ........................... | 623/2 |
| 5,078,739 A | * 1/1992 | Martin ........................... | 623/2 |
| 5,855,601 A | * 1/1999 | Bessler et al. .................. | 623/2 |
| 6,106,550 A | * 8/2000 | Magovern et al. ........... | 623/2.38 |
| 6,165,215 A | * 12/2000 | Rottenberg et al. ......... | 623/2.12 |
| 6,168,614 B1 | * 1/2001 | Andersen et al. ............. | 623/1 |
| 6,197,054 B1 | * 3/2001 | Hamblin, Jr. et al. ....... | 623/2.38 |
| 6,312,465 B1 | * 11/2001 | Griffin et al. ............... | 623/2.38 |
| 6,425,916 B1 | * 7/2002 | Garrison et al. ............ | 623/2.11 |

OTHER PUBLICATIONS

Syde A. Taheri et al.;"Experimental Prosthetic Vein Valve"; vol. 8, No. 1; p. 4.
Syde A. Taheri et al.; "Experimental Prosthetic Vein Valve"; vol. 156; p. 4.
Syde A. Taheri et al.; "Vein Valve Transplantation"; p. 4, pp. 278–281.
Syde A. Taheri et al.; "Vein Valve Tranplantation in Deep Venous Insufficiency"; p. 6, pp. 231–236.
Syde A. Taheri et al.; "Vein Valve Transplantation"; vol. 150; p. 2, pp. 201–202.
Syde A. Taheri et al.; "Results of Vein Valve Transplant after 6 years"; p. 4, Advances in Phlebology.

* cited by examiner

Primary Examiner—Bruce Snow
(74) Attorney, Agent, or Firm—Walter W. Duft

(57) ABSTRACT

A prosthetic valve adapted to be inserted into a blood vessel and held in a desired position therein. The valve includes an annular support ring having a longitudinal axis and defining a substantially circular central opening for passage of blood. The support ring has an outer wall that may be formed with a central annular depression. A leaflet is mounted on the support ring for pivotal movement between a closed position wherein the leaflet substantially blocks the central opening and an open position wherein blood is permitted through the opening. The valve is adapted to be inserted into the blood vessel such that the support ring longitudinal axis is substantially coincident with an axis of elongation of said blood vessel and held in such position in suitable fashion, such as by suturing or by way of a tightened cord holding a proximate portion of the blood vessel against the support outer wall if it is formed with an annular depression. The valve may additionally include a radial passage extending through the support ring and a stem extending radially outwardly from the radial passage. The stem has a central bore communicating with the radial passage and is adapted to extend through the wall of the blood vessel when the valve is mounted therein and provide an entry for introduction of anti-clotting agents and other materials proximate the valve. The valve may further include a plurality of external stabilizer elements adapted to extend through the wall of the blood vessel and provide locations for attaching various valve stabilizing assemblies. The support ring can also be made to be deformable or expandable to facilitate insertion and securement thereof in the vein.

15 Claims, 4 Drawing Sheets

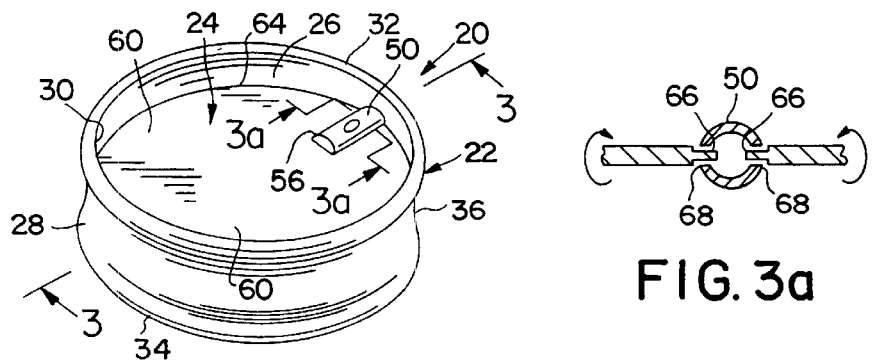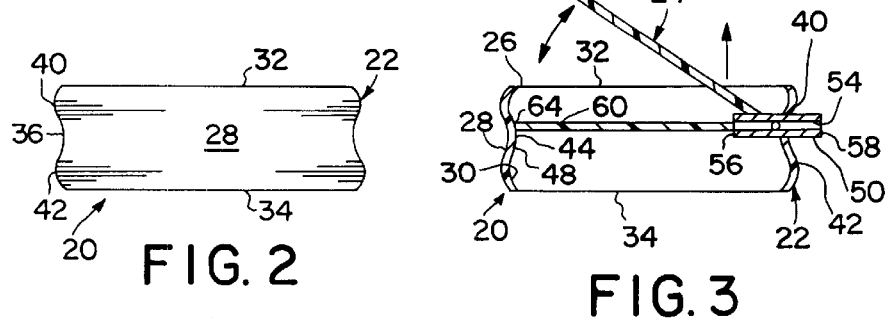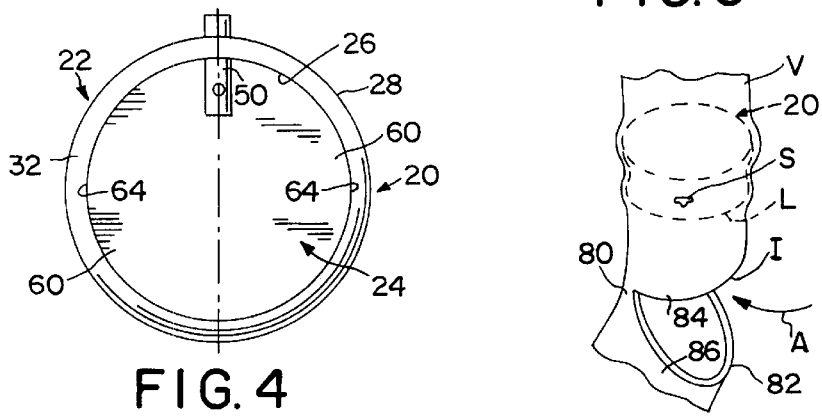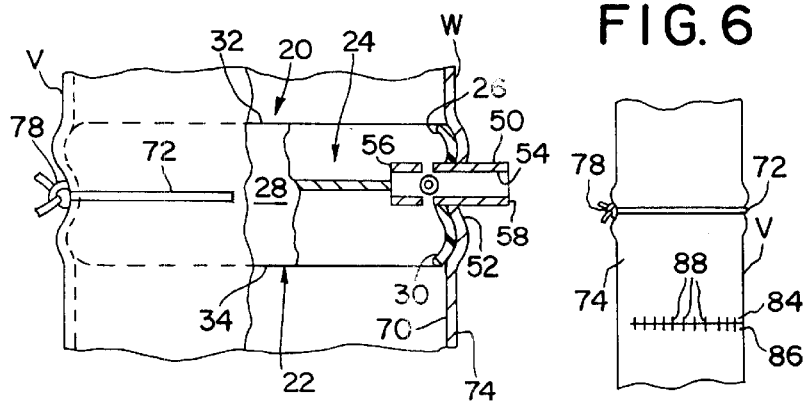

PROSTHETIC VEIN VALVE AND METHOD

BACKGROUND OF THE INVENTION

1. Field of the Invention

This invention relates to human venous insufficiency syndrome and the treatment thereof.

2. Description of the Prior Art

By way of background, venous insufficiency syndrome (VIS) is a chronic medical condition in which the ability of the venous system to maintain venous blood return to the heart and adequate venous pressure in the patient's extremities is impaired. Functional incompetency of the vein valves, due to venous valve prolapse ("floppy valve syndrome") and other conditions, is a common cause of this disorder.

Current methods of treating valvular incompetency include implantation of prosthetic vein valves. U.S. Pat. No. 4,851,001, issued to Applicant on Jul. 25, 1989, discloses such a prosthesis.

Recent re-evaluation of Applicant's patented prosthetic vein valve suggests that improvements can be made in the areas of valve functionality, valve securement, and blood clotting response. Applicant has identified a need for a new and improved prosthetic vein valve.

SUMMARY OF THE INVENTION

The foregoing problems are solved by an improved prosthetic valve adapted to be inserted into a blood vessel and held in a desired position therein. The valve includes an annular support ring having a longitudinal axis and defining a substantially circular central opening for passage of blood. The support ring has an outer wall that may be formed with a central annular depression. A leaflet is mounted on the support ring for pivotal movement between a closed position wherein the leaflet substantially blocks the central opening and an open position wherein blood is permitted through the opening. The valve is adapted to be inserted into the blood vessel such that the support ring longitudinal axis is substantially coincident with an axis of elongation of said blood vessel and held in such position in suitable fashion, such as by suturing or by way of a tightened cord holding a proximate portion of the blood vessel in the annular depression.

The valve may additionally include a radial passage extending through the support ring and a stem extending radially outwardly from the radial passage. The stem has a central bore communicating with the radial passage and is adapted to extend through the wall of the blood vessel when the valve is mounted therein and provide an entry for introduction of anti-clotting agents and other materials proximate the valve. The valve may further include a plurality of external stabilizer elements adapted to extend through the wall of the blood vessel and provide locations for attaching a valve stabilizing assembly. The stabilizing assembly may include a plurality of stabilizing arms that extend outwardly to engage body tissue surrounding the vein, or inwardly to engage the vein at a location which is spaced from the support ring. In the latter configuration, the stabilizing assembly may further include a stabilizing ring that extends around the vein at the spaced location.

The support ring can also be made to be deformable or thermally expandable to facilitate insertion and securement thereof in the vein. In a deformable configuration the support ring can be folded or radially compressed prior to insertion in the vein and then released when the valve is correctly positioned. In the thermally expandable configuration, the support ring can be thermally cooled prior to insertion in the vein and then allowed to expand when the valve is properly positioned.

The prosthetic valve of the invention can be implanted according to a novel method that includes providing a prosthetic valve as summarized above, forming an opening in the blood vessel at a location therein that is spaced from a location at which the valve is desired to be implanted, inserting the valve through the formed opening to such desired location at which the valve is to be implanted and orienting the valve so that the support ring longitudinal axis is substantially coincident with an axis of elongation of the blood vessel. The valve can be sutured. Or, a cord can be tightened about the outer wall of the blood vessel such that the proximate portion of the blood vessel is caused to assume the contour of the annular depression. The cord is then tied in the tightened condition to secure the support ring in a desired position.

BRIEF DESCRIPTION OF THE DRAWING

The foregoing and other features and advantages of the invention will be apparent from the following more particular description of preferred embodiments of the invention, as illustrated in the accompanying Drawing, in which:

FIG. 1 is a perspective view of an embodiment of a prosthetic valve in accordance with the present invention.

FIG. 2 is an elevational view of the FIG. 1 valve, as seen generally from one side in FIG. 1.

FIG. 3 is a cross-sectional view taken generally on line 3—3 of FIG. 1.

FIG. 3a is a fragmentary cross-sectional view taken generally on line 3a—3a of FIG. 1.

FIG. 4 is a plan view of the FIG. 1 valve, as seen from above in FIG. 2.

FIG. 5 is a fragmentary plan view, shown partially in section, of a blood vein within which the FIG. 1 valve is operatively positioned.

FIG. 6 is a fragmentary perspective view of a blood vein having an incision formed therein and through which the FIG. 1 valve is inserted when the valve is operatively positioned within the blood vein.

FIG. 7 is a fragmentary plan view of the FIG. 6 blood vein at the completion of the valve implantation process in accordance with the present invention.

DETAILED DESCRIPTION OF THE PREFERRED EMBODIMENT

Figure 8:
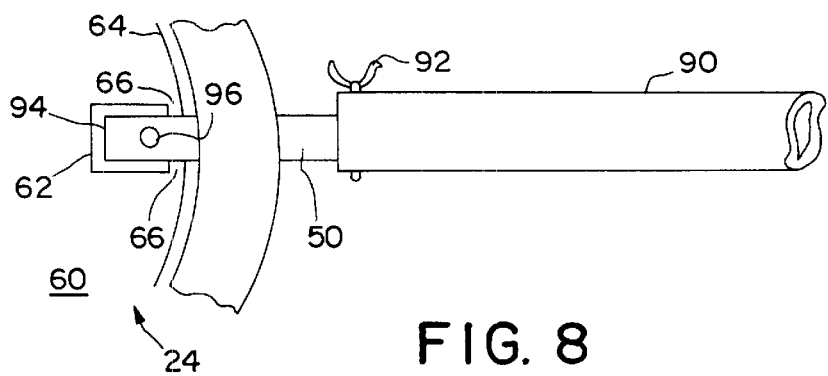
FIG. 8 is a detailed fragmentary plan view, as seen from above in FIG. 4, showing a stem portion of the FIG. 1 valve.

Turning now to the drawings in greater detail, FIG. 1 shows an embodiment, generally indicated by reference numeral 20, of a prosthetic valve in accordance with the present invention for implantation within a blood vein V (FIGS. 5 and 6). The valve 20 includes a generally annular support ring 22 and a leaflet, generally indicated at 24, connected to the support ring 22 for pivotal movement relative thereto. As will be explained in greater detail hereinafter, the support ring 22 has a longitudinal axis and defines a substantially circular-shaped central opening 26. A leaflet 24 is mounted on the support ring 22 for pivotal movement between a closed position wherein the leaflet substantially blocks the central opening 26 and an open position wherein blood is permitted through the opening. The leaflet 24 thereby cooperates with the support ring 22 to permit substantially one-directional or unidirectional flow through the support ring opening 26. Therefore, when the valve 20 is operatively positioned within a blood vein, the valve 20 permits flow of blood through the vein in only one direction.

With reference now to FIGS. 1–4, the support ring 22 has an outer wall 28, an inner wall 30 and two opposite ends 32 and 34 extending between the outer and inner walls 28 and 30. In accordance with the invention, the outer wall 28 of the support ring 22 is formed with a continuous central annular depression or groove 36 that faces generally radially outwardly of the ring 22. As will be described in more detail below, the groove 36 facilitates the securement of the valve 20 within the blood vein.

As best shown in FIG. 3, the outer wall 28 is contoured so as to define gentle undulations or waves as a path is traced therealong from one ring end 32 to the other ring end 34. Such undulations provide the groove 36 with relatively smoothly-contoured blunt edges 40, 42 on opposite sides thereof. More specifically, each of the groove edges 40 or 42 is rounded in shape, as viewed in the cross-sectional view of FIG. 3, and is devoid of sharp corners.

With reference still to FIG. 3, the inner wall 30 of the support ring 22 is contoured so as to be shaped generally complementarily to that of the outer wall 28 so that gentle undulations are defined in the inner wall 30 as the path is traced from one ring end 32 to the other ring end 34. The shape of each inner and outer wall 28 and 30 is symmetrical about a transverse radial midplane of the support ring 22. Furthermore, there is defined within the inner wall 30, a radially inwardly-directed annular bulge or projection 44 located generally midway between the ring ends 32 and 34 so that its inwardmost projecting portion, indicated at 48, is contained generally within the ring midplane 45. The support ring 22 can be constructed of any of a number of suitable materials, such as steel, platinum or titanium, or a non-metallic material such as a condensed carbon plastic of a type conventionally used for heart valves.

The ring outer wall 28 is preferably roughened or aspirated so as to feel relatively harsh to the touch. Inasmuch as the outer wall 28 is adapted to engage the inner wall of the blood vein in the manner explained hereinafter, the roughness of the outer wall 28 promotes a seating or clinging of the blood vein to the outer wall 28 so that the blood vein and outer wall 28 effectively adhere to or frictionally grip one another when positioned in operative engagement. An effective adherence reduces the likelihood that regions of the blood vein will become detached from the outer wall 28 in a manner creating pockets or voids within which blood is susceptible of accumulating or clotting.

With reference now to FIGS. 1, 3, and 4, the valve 20 includes a stem 50 that is press fit or otherwise secured in a radial passage 52 that extends through the support ring 22, from the outer wall 32 to the inner wall 30 where the central opening 26 is located. The stem 50 extends radially outwardly from the radial passage 52. It has a central bore 54 that communicates with the radial passage and respective interior and exterior ends 56 and 58. The bore 54 is also adapted to extend through the wall of the blood vessel V, as shown at W, when the valve 20 is mounted therein. As described in more detail below relative to FIG. 8, the bore 54 provides an entryway for introduction of anti-clotting agents and other materials proximate the valve 20.

The stem 46 is cylindrical in form and defines a first portion extending outside of the support ring 22, and a second portion extending into the central opening 26. As best shown in FIG. 3, the longitudinal axis of the stem 50 is oriented slightly offset to the radial midplane of the support ring 22 so as to be positioned slightly closer to the ring end 32 than the ring end 34.

The leaflet 24 is hingedly joined to the stem 50 for pivotal movement between an open condition to a closed condition wherein it seats on the bulge portion 44 of the support ring 22, as shown in FIG. 3. As best shown in FIG. 4, the leaflet is a thin disk having a substantially circular body 60 with a generally U-shaped cutout 62 and an arcuate edge 64.

FIG. 3a shows an exemplary hinge connection that may be used to mount the leaflet 24 to the stem 50. The cutout 62 should be of such size as to be movably yet snugly received about the stem 50 to minimize blood back flow through the valve. FIG. 8 shows the pivotal connection between the leaflet 24 and the stem 50 in more detail. Note that the spacing between the components has been greatly exaggerated in order to more clearly illustrate their manner of interconnection. Disposed along each side of the cutout 62 is a pivot pin 66. As also shown in FIG. 3a, each pivot pin 66 extends into a mating hole 68 formed on opposing sides of the stem 50. The holes 68 are in coaxial relationship with each other and, together with the pivot pins 66, define a pivotal axis for the leaflet 24. Note that this pivotal axis should lie at the arcuate edge 64 of the leaflet 24, so that the leaflet will pivot away from the bulge portion 44 of the support 22 ring and not interfere therewith. The leaflet 24 is constructed of a suitable material, such as steel, platinum or titanium. It may also be constructed from a non-metallic material such as a condensed carbon plastic of a type conventionally used for heart valves. The pivot pins 66 may be formed integrally therewith or they may be attached thereto as separate components.

With reference again to FIG. 3, the leaflet 24 is sized so that it fully spans the support ring opening 26 and is prevented by the bulge 44, which effectively defines a valve seat, from pivoting from the closed position in FIG. 3 toward the ring end 34. To this end, the diameter of the leaflet 24 as viewed in the plan view of FIG. 4 is slightly larger than the diameter of the support ring opening 26, as measured across the radial midplane thereof at the location of the inwardmost projection 48. Moreover, as indicated above, the stem 46, to which the leaflet 24 is pivotally mounted, is arranged to one side of the support ring midplane, closer to the ring end 32.

Thus, due to the pivotal connection between the leaflet 24 and the stem 46, the leaflet 24 is only permitted to pivot relative to the support ring 22 between the FIG. 3 closed condition, at which each arcuate edge 64 of the leaflet 24 rests in engagement with the surface of the bulge 44, and the FIG. 3 open condition at which the plane of the arcuate edge 64 is arranged angularly with respect to the radial midplane of the ring 22.

It will be seen that when the leaflet 26 is positioned in the FIG. 3 open condition, the support ring opening 26 is opened so as to permit substantially unrestricted flow of a fluid in the direction of the parallel arrows B and C. Conversely, when the leaflet 26 is positioned in the FIG. 3 closed condition, the opening 26 of the support ring 22 is shut off so as to prevent flow of fluid therethrough.

With reference now to FIG. 5, the valve 20 is positionable within a blood vein V so that its support ring 22 is oriented generally within a radial plane of the blood vein V and so that the inner wall, indicated at 70, of the blood vein closely surrounds the ring outer surface 28. The stem 50 will extend through an opening in the wall of the blood vein, which can be formed prior to valve insertion as further described below. In such a position, the valve 20 is securable by means of a cord 72 tied about the outer wall, indicated at 74 of the blood vein V and tightened within the groove 36. Opposite ends of the cord 72 are tied in a knot 78. The cord 72 is constructed of a suitable material, such as silk, and is of sufficient length to encompass the support ring 22 when tied thereabout.

With the valve operatively positioned and secured within the blood vein V by means of the cord 72, the inner wall 70 of the blood vein V lies in substantial conformity with the shape of the outer wall 28 of the support ring 22. To this end, the minimum diameter of the support ring outer wall 28 is at least as great as the diameter of the vein inner wall 70 so that the engagement between the inner wall 70 and the ring outer wall 28 is continuous from one end 32 of the support ring 22 to the other ring end 34. Such conformity and engagement of the inner wall 70 with the ring outer wall 28 reduces the likelihood that voids or regions will develop between the inner wall 70 and the ring outer wall 28 within which blood is likely to accumulate and clot. More specifically, the blood vein inner wall 70 is conformed to the gentle undulations in the ring outer wall 28 and is thereby not required to define a sharp corner as a path is traced from one ring end 32 to the other ring end 34. Furthermore and related to the fact that the ring outer wall 28 is devoid of sharp corners, the wall of the blood vein V is not appreciably deformed about the outer wall 28 when the cord 72 is tightened about the blood vein V.

In order to implant the valve 20 within the blood vein V, an opening 82 can be formed in the blood vessel to permit the insertion of the valve 20 within. Such an opening 82 can be formed by incising or making an appropriately-sized incision I across the blood vein V by means of a knife (not shown) or similar cutting tool. The incision I is oriented within a radial plane of the blood vein V and extends for a substantial distance, but not entirely around, the circumference of the blood vein. Thus, the blood vein V remains joined at the incision I by means of an uncut portion 80. Furthermore and in accordance with the present invention, the incision I is spaced longitudinally from the radial plane or location, indicated at L, at which the valve 20 is desired to be secured. At this location, there is further formed a small slit S which is of sufficient minimum length to accommodate the stem 50. In particular, the length of the slit S should be equal to or greater than the outside diameter of the stem 50. The slit S can extend transversely relative to the axis of elongation of the vein V or it may extend parallel thereto. Although a single slit is shown in FIG. 6, it will be appreciated that a second slit may be formed that intersects the slit S and is perpendicular thereto, such that the two slits form a cross configuration. Moreover, instead of a slit S, a small hole could be formed to receive the stem 50.

Once the incision L and the slit S are formed, the valve 20 is inserted through the opening 82 in the direction of the arrow A and directed along the length of the blood vein V until the location L is reached. At that point, the valve 20 is manipulated so that its support ring 22 is arranged within a radial plane of the blood vein V and the stem 50 extends through the slit S. During insertion of the valve 20 within the blood vein V, care should be taken to ensure that the ring end 32 is oriented on the downstream-side of the blood vein location L so that the valve 20 permits blood flow through the blood vein in the direction in which blood flow is desired.

To secure the valve 20 within the blood vein, the cord 72 is provided and then tied around the outer wall of the blood vein V and support ring 22 so that the inner wall 70 of the blood vein conforms substantially to the ring outer surface 28. To this end, the cord 72 is wrapped around the blood vein V and tightened within the annular groove 36 and tied in a knot 78. The valve 20 is thereby prevented from shifting or moving relative to and along the length of the blood vein V as the blood vein walls are secured between the cord 72 and the ring outer surface 36.

Upon securing the valve 20 within the blood vein V by means of the cord 72, the opening 82 is closed. To this end, and with reference to FIG. 7, the opposite sides, indicated at 84 and 86, of the incision I are positioned adjacent one another and stitched together by means of stitches 88. If necessary, a stitch can also be placed on each side of the stem 50 to close the slit S.

With the valve 20 secured in the blood vein V as described above, the stem 50 will extend externally of the vein. As shown in FIG. 8, this will provide an access point for the introduction of medicaments, anti-clotting agents (e.g., Heparin irrigation), endothelial cell growth promoters (e.g., autologous cell cultures), Tissue Plasminogen Activator (TPA) and other materials to the valve situs. To this end, a small catheter 90 may be temporarily secured to the stem 50 using a tie 92 or other suitable means. Material introduced into the catheter 90 can be made to exit the stem 50 at one of several points. For example, the bore 54 of the stem 50 may extend to a central opening 94 of the end 56 of the stem. Alternatively or in addition thereto, the stem may be provided with one or more lateral openings 96. Using the access pathway provided by the stem and the catheter 90, conditions such as neointimal hyperplasia can be monitored and Heparin treatment applied if endothelial growth becomes excessive. It will also be seen that the pathway provided by the stem 50 and the catheter 90 permits the introduction of diagnostic and monitoring equipment, such as direct vision equipment and the like. A medical practitioner could thus, for example, obtain a valvulogram for use in observing valve function and for detection of possible clot formation.

Figure 9:
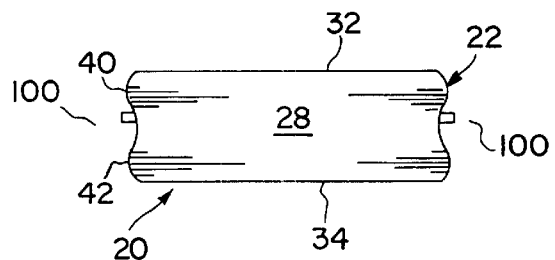
FIG. 9 is an elevational view of a modified version of the FIG. 1 valve in which the valve includes stabilizer elements, as seen generally from one side of the modified valve.
Figure 10:
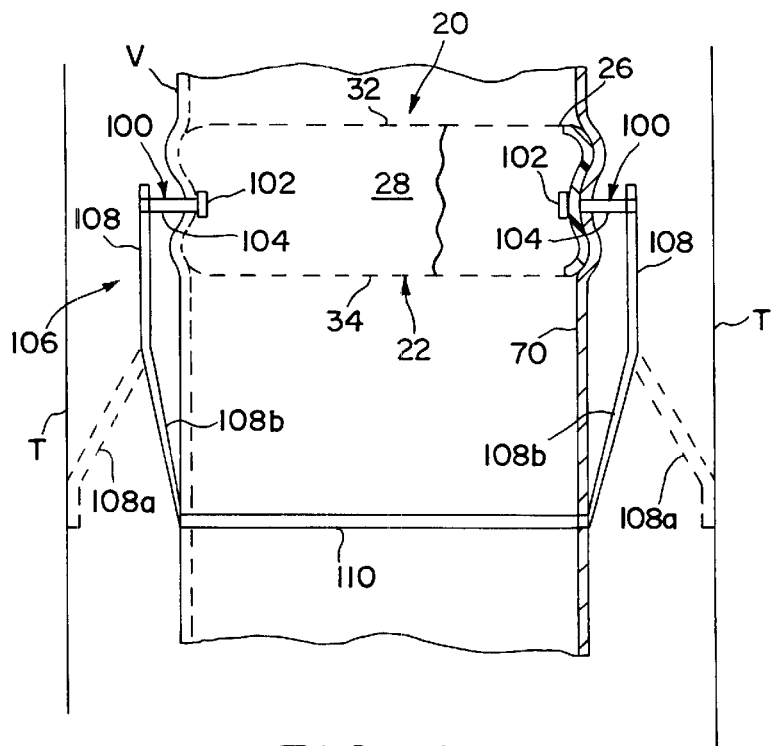
FIG. 10 is a fragmentary plan view, shown partially in section, of a blood vein within which the FIG. 9 modified valve is operatively positioned.

Turning now to FIGS. 9 and 10 an alternative embodiment of the valve 20 is shown in which the valve further includes a plurality of external stabilizer elements 100. The stabilizer elements 100 can be formed integrally with the support ring 22, or they may be either fixedly or movably connected thereto. In one configuration, the stabilizer elements 100 are relatively small in size (e.g., less than the vein wall thickness) so that they extend into, but not through the blood vein V. The stabilizer elements 100 will then serve to engage and grip the inner wall of the blood vein V, thereby restraining the valve 20 from rotating therein. In an alternative configuration, the stabilizer elements 100 are sized to extend through the wall of the blood vein V, as shown in FIG. 10. Note that FIG. 10 also illustrates the stabilizer elements 100 being formed as pins that have a head 102 at one end and a shaft 104 that is received through the support ring 22. Note that the shaft 104 could be made to be slidably received through the support ring 22, in which case the stabilizer elements 100 could be retracted during valve insertion and thereafter extended for valve securement.

In the configuration of FIG. 10, the stabilizer elements 100 are used to provide locations for attaching an external valve stabilizing assembly, shown generally at 106. The stabilizing assembly 106 includes at least two stabilizing arms 108. These arms may be configured in several ways. For example, as shown at 108a, the stabilizing arms 108 could be configured to extend outwardly for engaging body tissue T that surrounds the vein V. Alternatively, as shown at 108b, the stabilizing arms 108 could be configured to extend inwardly to engage the vein V at a location which is spaced from the support ring. In this configuration, the stabilizing assembly 106 may further include a stabilizing ring 110 that extends around the vein at the spaced location.

Note that the stabilizing arms 106 need to be removably attachable to the stabilizer elements 100 so that they can be mounted thereon following valve installation. Moreover, if the stabilizer assembly 106 uses the stabilizing ring 110, the ring will have to be openable so that it can be placed around the vein V. Otherwise, the vein V would need to be completely severed in order to receive the stabilizing ring 110. Another option would be to construct the stabilizer ring 110 as two semi-circular elements that are each mounted to one (or more) of the stabilizing arms 108 and brought into contact with the vein V from either side thereof.

In order to facilitate insertion and securement of a valve 20 having stabilizer elements 100 thereon, the support ring 22 can be made to be deformable or thermally expandable, such that the support ring 22 can be reduced in overall size during the valve insertion process and then increased in size when securement is desired. In a deformable configuration, the support ring 22 could be made from a suitably flexible polymer that can be folded or radially compressed prior to insertion of the valve 20 in the vein V. Note that this insertion method will be particularly useful when the valve 20 is equipped with the stabilizing elements 100. By folding or radially compressing the valve 20, the stabilizer elements 100 can be positioned so that they will not catch on the vein wall during insertion. When the valve 20 is correctly positioned, the support ring 22 can be released to allow the stabilizer elements 100 to engage (or pierce) the vein wall. In the thermally expandable configuration, the support ring 22 could be made from a plastic coated metal that can be thermally cooled prior to insertion in the vein and then allowed to expand (by drawing heat from the warm blood) when the valve is properly positioned.

Note that use of the stabilizer 100 elements may obviate having to tie the valve 20 to the vein V. This would in turn facilitate percutaneous introduction of the valve, via the jugular vein for example.

Figure 11:
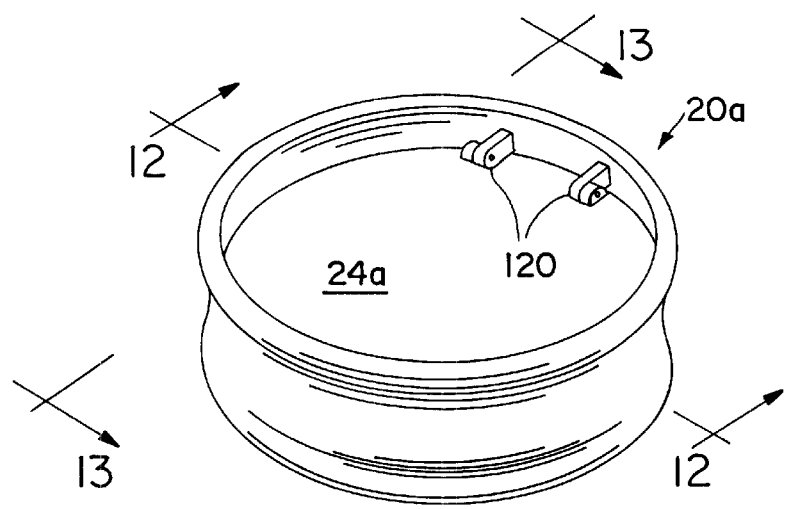
FIG. 11 is a perspective view of another embodiment of a prosthetic valve in accordance with the present invention.
Figure 12:
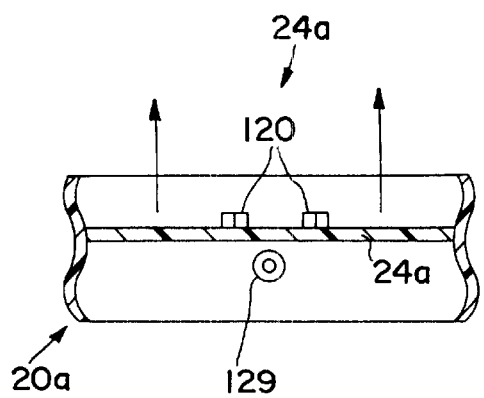
FIG. 12 is a cross-sectional view taken generally on line 12—12 of FIG. 11.
Figure 13:
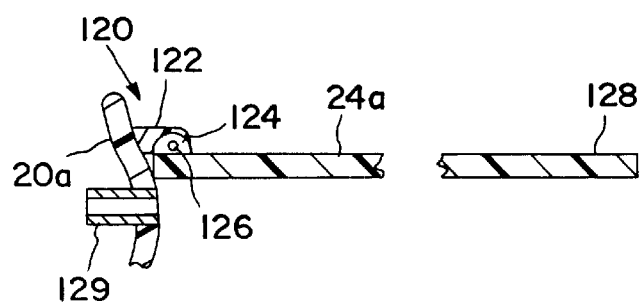
FIG. 13 is an enlarged fragmentary cross-sectional view taken generally on line 13—13 of FIG. 11.

Turning now to FIGS. 11 and 12, a further alternative embodiment of the valve 20a is shown in which a leaflet 24a is directly pivotally mounted to a support ring 22a. Except for the manner in which they pivotally interconnect, the support ring 22a and the leaflet 24a may be identical in all respects to the support ring 22 and the leaflet 24 described above. The pivotal attachment between the support ring 22a and the leaflet 24a is provided by a pair of spaced hinges 120. The hinges 120 can be constructed in a variety of ways. For example, as shown in FIG. 13, each hinge 120 may include a first tab member 122 attached to the inner wall of the support ring 22a, a second tab member 124 attached to the top of the leaflet 24a, and an interconnecting pin 126. Note that because the leaflet 24a connects directly to the support ring 22a, no stem is required in this embodiment, although it could be added if desired. If a stem is used in the embodiment of FIGS. 11, 12 and 13, its interior end (see e.g., element 56 in FIG. 3) will preferably not protrude into area of the central opening of the support ring 22a, and will terminate at the support ring's inner wall. See, for example, the stem 129 of FIGS. 12 and 13. As a further enhancement to the leaflet 24a, FIG. 13 shows that the side of the leaflet that is opposite the hinges 120, as shown at 128, could be made thicker so that this side of the leaflet is heavier than the side that mounts the hinges. This non-uniform weight distribution of the leaflet 24a will tend to force the valve closed, due to gravity, thus assisting in valve operation. Other weight distribution methods could also be used, such as by adding a small weight to the leaflet 24a rather than changing its thickness.

Figure 14:
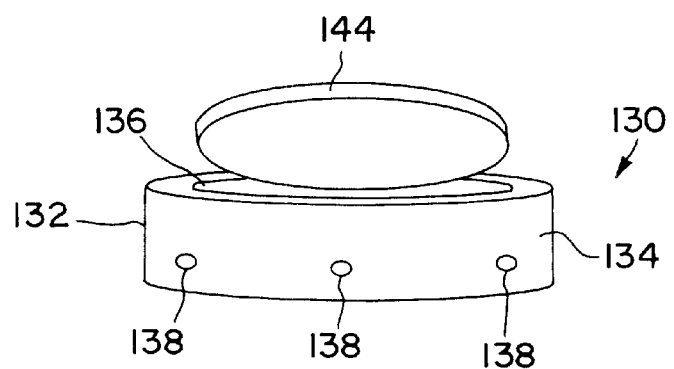
FIG. 14 is a perspective view of another embodiment of a prosthetic valve in accordance with the present invention.
Figure 15:
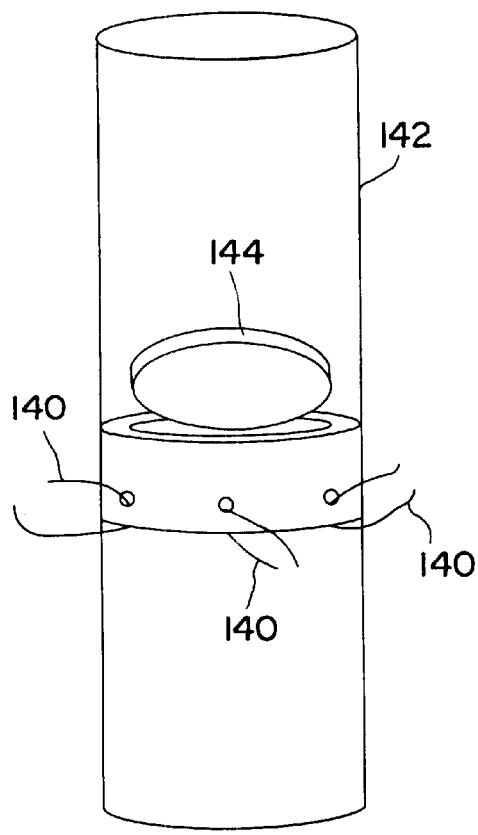
FIG. 15 is a perspective view of the vein valve of FIG. 14 in a blood vein.

In a still further embodiment of the invention, shown in FIGS. 14 and 15, a vein valve 130 is adapted to be sutured to a vein wall instead of being attached thereto in the manner of the previous embodiments. To that end, the valve 130 is provided with an annular ring 132 that has substantially flat inner and outer walls 134 and 136. Extending through the ring 132 are a plurality of small openings 138 that are adapted to receive sutures 140 when the valve 130 is positioned in a blood vein 142. Element 144 shows a valve leaflet in an open position.

Accordingly, a prosthetic vein valve and related method have been disclosed. While various embodiments of the invention have been described, it should be apparent that many variations and alternative embodiments could be implemented in accordance with the invention. It is understood, therefore, that the invention is not to be in any way limited except in accordance with the spirit of the appended claims and their equivalents.

What is claimed is:

1. A prosthetic valve adapted to be inserted into a blood vessel and held in a desired position therein, comprising:
   an annular support ring having a longitudinal axis and defining a substantially circular central opening for passage of blood;
   an outer wall on said support ring, said outer wall having a central annular depression therein;
   a leaflet mounted on said support ring for pivotal movement between a closed position wherein said leaflet substantially blocks said central opening and an open position wherein blood is permitted through said opening; and
   access point means on said outer wall for introduction of materials to a blood vessel situs where said valve is to be situated;
   whereby said valve may be inserted into said blood vessel such that said support ring longitudinal axis is substantially coincident with an axis of elongation of said blood vessel and held in such position by way of a tightened cord holding a proximate portion of said blood vessel in said annular depression.

2. The prosthetic valve of claim 1 wherein said access point means comprises a radial passage in said support ring, said passage extending from said outer wall to said central opening, and a stem extending radially outwardly from said radial passage, said stem having a central bore communicating with said radial passage and being adapted to extend through the wall of said blood vessel when said valve is mounted therein and provide an entry for introduction of anti-clotting agents and other materials proximate said valve.

3. The prosthetic valve of claim 2 wherein said stem extends into said central opening and pivotally mounts said leaflet.

4. The prosthetic valve of claim 3 wherein said stem includes one or more ports where said stem extends into said central opening, said ports communicating with said central bore and allowing said anti-clotting agents and other materials to be placed proximate said central opening.

5. The prosthetic valve of claim 1 wherein said valve further includes a plurality of external stabilizer elements adapted to engage through the wall of said blood vessel and provide additional securement of said valve thereto.

6. The prosthetic valve of claim 5 wherein said stabilizer elements extend through the wall of said blood vessel and said valve further includes a stabilizing assembly mounted to said stabilizer elements.

7. The prosthetic valve of claim 6 wherein said stabilizing assembly includes a plurality of stabilizing arms connected to said stabilizer elements.

8. The prosthetic valve of claim 7 wherein said stabilizing arms are oriented inwardly for engaging said vein.

9. The prosthetic valve of claim 7 wherein said stabilizing arms are oriented outwardly for engaging tissue surrounding said vein.

10. The prosthetic valve of claim 7 wherein said stabilizing assembly further includes a ring mounted to said stabilizing arms and adapted to be secured around said vein in spaced relationship with said valve.

11. The prosthetic valve of claim 1 wherein said support ring is made from a deformable material that allows said valve to be deformed to facilitate insertion into said vein.

12. The prosthetic valve of claim 1 wherein said support ring is radially compressible and sized larger than said vein such that said ring is under radial compression when positioned in said vein to help stabilize said valve.

13. The prosthetic valve of claim 1 wherein said support ring is formed from a thermally expandable material that expands radially when said valve is positioned in said vein to help stabilize said valve.

14. The prosthetic valve of claim 13 wherein thermally expandable material is a plastic coated metal.

15. A prosthetic valve adapted to be inserted into a blood vessel and held in a desired position therein, comprising:

an annular support ring having a longitudinal axis and defining a substantially circular central opening for passage of blood;

a radial passage in said support ring, said passage extending from an outer wall of said support ring to said central opening;

a leaflet mounted on said support ring for pivotal movement between a closed position wherein said leaflet substantially blocks said central opening and an open position wherein blood is permitted through said opening, said leaflet being weighted at locations thereof that are remote from its point of mounting on said support ring to assist in valve closure;

a stem extending radially outwardly from said support ring radial passage, said stem having a central bore communicating with said radial passage and being adapted to extend through the wall of said blood vessel when said valve is mounted therein and provide an entry for introduction of anti-clotting agents and other materials proximate said valve; and whereby said valve may be inserted into said blood vessel such that said support ring longitudinal axis is substantially coincident with an axis of elongation of said blood vessel and held in such position by appropriate attachment to said blood vessel.

* * * * *